United States Patent

Ibi et al.

[11] Patent Number: 5,302,754
[45] Date of Patent: Apr. 12, 1994

[54] PURIFICATION PROCESS OF METHACRYLAMIDE

[75] Inventors: Akira Ibi; Toshimi Ogata; Yoshihiro Nodate; Takayuki Kageyama, all of Chiba, Japan

[73] Assignee: Mitsui Toatsu Chemicals, Inc., Tokyo, Japan

[21] Appl. No.: 961,020

[22] Filed: Oct. 14, 1992

Related U.S. Application Data

[63] Continuation of Ser. No. 712,109, Jun. 7, 1991, abandoned.

[30] Foreign Application Priority Data

Jun. 13, 1990 [JP] Japan ................... 2-152710
Jun. 28, 1990 [JP] Japan ................... 2-168374

[51] Int. Cl.$^5$ ........................... C07C 233/09
[52] U.S. Cl. ................................. 564/206
[58] Field of Search ........................ 564/206

[56] References Cited

U.S. PATENT DOCUMENTS

| | | | |
|---|---|---|---|
| 2,865,960 | 12/1958 | Shearer et al. | 564/206 |
| 3,549,706 | 12/1970 | Takaki et al. | 564/206 |
| 3,666,809 | 5/1972 | Okuno et al. | 564/206 |
| 4,010,142 | 3/1977 | Hurlock et al. | 564/206 |
| 4,345,101 | 8/1982 | Asano et al. | 564/206 |
| 4,465,856 | 8/1984 | Horiuchi et al. | 564/206 |

FOREIGN PATENT DOCUMENTS 2063529 7/1971 Fed. Rep. of Germany.
7006747 11/1970 Netherlands ................... 564/206

Primary Examiner—Glennon H. Hollrah
Assistant Examiner—Shailendra Kumar
Attorney, Agent, or Firm—Burns, Doane, Swecker & Mathis

[57] ABSTRACT

A purification process of crude methacrylamide by recrystallization from an aqueous methacrylamide solution, comprising the steps of conducting crystallization by adjusting the hydrogen ion concentration of the aqueous methacrylamide solution to pH 8 or more, separating a methacrylamide crystal, adjusting 5% by weight or more of resulting mother liquor to pH 5 or less, separating precipitated insoluble matter, and reusing thus-treated mother liquor, is provided.

The high quality methacrylamide crystal thus obtained is excellent in Hazen number, purity and transparency of a methanol solution and suitable for uses such as windshield glasses.

4 Claims, No Drawings

PURIFICATION PROCESS OF METHACRYLAMIDE

This application is a continuation of application Ser. No. 07/712,109, filed Jun. 7, 1991, now abandoned.

BACKGROUND OF THE INVENTION a) Field of the Invention

The present invention relates to a process for preparing high purity methacrylamide suitable for use in modifiers in the field of windshield glasses, photographic films and coagulating agents by purification of an aqueous crude methacrylamide solution.

b) Description of the Prior Art

Many processes have been known for the preparation of methacrylamide.

These processes are, for example, a process for reacting acetone cyanhydrin (hereinafter referred to as ACH) with sulfuric acid and neutralizing the resulting methacrylamide sulfate to obtain methacrylamide; and a process for hydrating methacrylonitrile to obtain methacrylamide.

The methacrylamide prepared by the above processes are satisfactory for use in the field of fiber modifiers and the raw material for preparing emulsion of coating and adhesive.

The above methacrylamide, however, cannot be used in view of quality for windshield glasses and other applications. High degree of transparency is required for many resin products used for these applications, and hence contamination of a trace amount of impurity such as polymer leads to serious deterioration of quality in these products.

Purification steps are required for preparing the high purity methacrylamide and recrystallization is the most practical process of purification. As a recrystallization process, for example, Japanese Patent 50666 (1984) (U.S. Pat. No. 4,465,856) discloses crystallization under alkaline conditions.

However, in the purification of methacrylamide by recrystallization, the mother liquor obtained by separating the crystal is preferably recycled as a raw material to the next crystallization step. Repeated recycling leads to a problem of rapid deterioration in the quality of methacrylamide.

In order to inhibit deterioration of quality, the mother liquor is often treated with activated carbon. The treatment, however, cannot maintain satisfactory quality of methacrylamide and a portion of the mother liquor must be discharged out of the system.

SUMMARY OF THE INVENTION

An object of the present invention is to provide a process for preparing purified methacrylamide which can also be used for resin products requiring high degree of transparency.

Another object of the invention is to provide a process for purifying methacrylamide from an aqueous methacrylamide solution by recrystallization process.

A further object of the present invention is to provide a process for effectively recycling the mother liquor formed in the recrystallization.

The above objects can be satisfied with a purification process of crude methacrylamide by recrystallization from an aqueous methacrylamide solution, comprising the steps of conducting crystallization by adjusting the hydrogen ion concentration of the aqueous methacrylamide solution to pH 8 or more, separating a methacrylamide crystal, adjusting 5% by weight or more of resulting mother liquor to pH 5 or less, separating precipitated insoluble matter, and reusing thus-treated mother liquor.

The methacrylamide purified by the above process of the invention has extremely high quality and is suitable for uses such as windshield glasses.

DETAILED DESCRIPTION OF THE INVENTION

Methacrylamide prepared by any process can be used for the raw material of recrystallization in the process of the invention.

The raw material commonly used is crude methacrylamide obtained by reacting ACH with concentrated sulfuric acid and neutralizing the resultant methacrylamide sulfate with alkali such as ammonia.

The purification process of methacrylamide in the invention will be illustrated hereinafter.

The purification process of methacrylamide in the invention is fundamentally the same as a usual recrystallization process and consists of dissolution of crude methacrylamide in water, pH adjustment of aqueous crude methacrylamide solution, crystallization, centrifugation and drying.

In other words, methacrylamide sulfate obtained by amidation reaction of ACH with sulfuric acid is neutralized with ammonia, and precipitated crystal is centrifuged to obtain crystal of crude methacrylamide. The crude methacrylamide is dissolved, adjusted to pH 8 or more, crystallized and the crystal is separated from mother liquor. The crystal was dried to obtain purified crystal.

In the above steps, water is used as a solvent for dissolving the crystal of crude methacrylamide.

Dissolution temperature is in the range of from 30° to 60° C., preferably in the range of from 40° to 55° C. in view of quality of the product and efficiency of crystallization. Solubility of methacrylamide in water is from 25 to 70% by weight at a temperature of from 30° to 60° C. and from 35 to 59% by weight at a temperature of from 40° to 55° C. In consideration of liquid transfer to the next step, the conditions of 50° C. in temperature and from 35 to 50% by weight in methacrylamide concentration are preferred.

Successively, hydrogen ion concentration of the above aqueous methacrylamide solution is adjusted to an alkaline condition, that is, to pH 8 or more, preferably in the range of from pH 8 to pH 13.

No particular restriction is imposed on the alkali used for pH control. Any kind of alkali can be used. Commonly used alkali includes hydroxide and carbonate of alkali metals and alkali earth metals; and ammonia. Sodium hydroxide and potassium hydroxide are preferably used in particular.

In the next step, methacrylamide is crystallized from an aqueous methacrylamide solution.

Any common process can be used for the crystallization of the invention. Cooling crystallization or concentrating crystallization is preferred. Crystallization can be carried out both by batch process and by continuous process.

Crystallized methacrylamide is separated from the solution by centrifugation, and the separated crystal is dried by usual methods to prepare the product.

On the other hand, according to the information obtained by the present inventors, separated mother liquor contains polymer which was previously included in the raw material methacrylamide and a small amount of polymer formed in the crystallization step. Consequently, repeated use of the mother liquor in the dissolution step of crude methacrylamide by conventional processes has been found to cause rapid deterioration of product quality.

Accordingly, the present inventors have discovered that the polymers contained in the mother liquor rapidly decrease in solubility and precipitate under acidic conditions. They have employed a process for precipitating the polymers dissolved in the mother liquor by adjusting the hydrogen ion concentration of the mother liquor to pH 5 or less.

The pH control of the mother liquor can be conducted by using common mineral acids or organic acids. Particularly preferred acids are sulfuric acid and hydrochloric acid. It is required to reduce pH to 5 or less. It is also possible to adjust pH to a strongly acidic condition. However, such condition unfavorably leads to unstable mother liquor. Hence, the range of from pH 1 to pH 4 is more preferred.

The amount of mother liquor to be used for pH control may be the whole amount. The pH control in portion can also maintain quality of the product. Product quality can be maintained by treating the mother liquor in an amount of preferably 5% by weight or more, more preferably from 10 to 80% by weight.

Insoluble matter such as polymers which are precipitated by pH control of the mother liquor can be separated by using common separating equipment such as a filter press, cartridge type line filter and centrifuge.

The liquid obtained by removing the insoluble matter is recycled to a suitable step and reused. The present invention, however, can more preferably provide the following two processes.

The first process is to separate the precipitated insoluble matter and to recycle the residual liquid to the neutralization step of methacrylamide sulfate. The second process is to separate the precipitated insoluble matter, to remove the anionic component, and successively to recycle the residual liquid to the next crystallization step, more practically, to the dissolution step of crude methacrylamide.

In the first process, from 5 to 100% by weight, preferably from 10 to 80% by weight of the mother liquor is recycled to the neutralization step of methacrylamide sulfate after neutralization and separation of the insoluble matter. The remainder, that is, from 95 to 0% by weight, preferably from 90 to 20% by weight of the mother liquor is not subjected to pH adjustment and is recycled as intact to the crude methacrylamide dissolution step having pH 8 or more. Methacrylamide sulfate is usually maintained at pH 5 or less in the neutralization step and hence the liquid obtained by separating the insoluble matter which was precipitated by pH adjustment, can be recycled as such to the neutralization step.

In the second process, the insoluble matter is separated from the mother liquor and successively anionic component is removed from the resulting liquid preferably by using anion exchange resin.

The anion exchange resin which can be used is strongly basic and weakly basic anion exchange resin, and includes, for example, Diaion SA-10A, PA-312 and PA-316 (Trade Mark of Mitsubishi Kasei); Amberlite IRA-401 and IRA-900 (Trade Mark of Japan Organo); and Lewatit MP-500 (Trade Mark of Bayer AG).

Both fluidization method and immersion method can be carried out for the treatment of the resulting liquid with the anion exchange resin. The fluidization method is preferred because the liquid is treated in a packed column. In carrying out the step, usual conditions can be used for treatment time and flow rate of the liquid. No particular limitation is placed on the treatment temperature so long as the temperature does not exceed heat resistance of the anion exchange resin.

The mother liquor can be recycled after the above treatment to the next crystallization step to be used as a part of the dissolving solution. In the practice of the process, the whole amount of mother liquor may be adjusted to pH 5 or less and recycled to the dissolution step of crude methacrylamide. Alternatively, as in the first process above, a portion of the mother liquor may be subjected to pH adjustment, precipitated matter is removed, and the resulting liquid is treated with anion exchange resin and recycled to the dissolution step of crude methacrylamide. The remainder of the mother liquor may be recycled as intact to the dissolution step of crude methacrylamide.

The present invention will hereinafter be illustrated further in detail by way of examples. In the examples, "%" is on the basis of weight unless otherwise noted. Methacrylamide obtained was analyzed by the following methods. Purity:

Purity was determined by measuring the double bond value through a bromine addition method, analyzing methacrylic acid through gas chromatography, and correcting these values.

Hazen Number (APHA)

Hazen number (APHA) was determined by comparison with the standard color in a 10% aqueous methacrylamide solution.

Moisture

Moisture content was measured by Karl Fischer's method.

Transparency

Transparency was measured in a solution containing 100 g of methacrylamide in 400 ml of methanol with a transparency tester having a maximum graduation of 50 cm in accordance with JIS K-0102.

EXAMPLE 1

Synthesis of Crude Methacrylamide Raw Material

Methacrylamide sulfate was prepared by reacting ACH with sulfuric acid at 160° C. in a sulfuric acid/ACH mole ratio of 1.7. Amidation rate was 93.5 mol %.

To a 3 l flask equipped with a stirrer, 974 ml of water was charged and 739 g of the methacrylamide sulfate was added dropwise at a temperature of 30° C. or less. Successively, gaseous ammonia was blown through the reaction mixture at temperature of 40°–45° C. until the reaction mixture was neutralized to pH 2.5.

The neutralized slurry was centrifuged and the crystal obtained was washed with 240 ml of cold water. The hydrate crystal thus obtained was dried in a rotary evaporator at 70° C. for 20 minutes under reduced pressure of 50 mmHg.

Crude methacrylamide thus obtained had purity of 99.3%, Hazen number (APHA) of 20, and transparency of 3.

Any of the crude methacrylamide to be used for the raw material of crystallization was prepared by the same process.

Crystallization

To a 1 l flask equipped with a stirrer, 220 ml of water was charged and warmed to 50° C. The crude methacrylamide obtained above was added so as to obtain a concentration of 47%. To the solution thus obtained, a 48% aqueous sodium hydroxide solution was added to adjust the solution to pH 10.

The aqueous methacrylamide solution obtained was allowed to cool for 30 minutes, and thereafter cooled to 15° C. over 30 minutes to precipitate the crystal.

The resulting slurry was sufficiently centrifuge-dehydrated and the crystal was washed by spraying 40 ml of cold water.

The hydrate crystal obtained was dryed in a rotary evaporator at 60° C. under air blowing to obtain 143 g of pure methacrylamide.

The pure methacrylamide had purity of 99.5% or more, moisture content of 0.4%, Hazen number (APHA) of 10 or less, and transparency of 50 or more.

In addition, the mother liquor obtained was 270 g and had a methacrylamide concentration of 17%.

The whole amount of the mother liquor was charged to a 1 l flask equipped with a stirrer and adjusted to pH 3 by using 98% sulfuric acid. Precipitated insoluble matter was filtered off with a nutsche fitted with a celite-precoated filter paper to obtain 255 g of treated mother liquor.

The whole amount of the treated mother liquor was recycled to the preparation step of crude methacrylamide.

Synthesis-1: (crude methacrylamide raw material)

To a 3 l flask equipped with a stirrer, 710 ml of water and 225 g of the treated mother liquor were charged, and 603 g of the methacrylamide sulfate was added dropwise at the temperature of 30° C. or less. Successively, gaseous ammonia was blown through the reaction mixture while maintaining the temperature from 40° to 45° C. until the reaction mixture was neutralized to pH 2.5.

The slurry obtained was centrifuged and the crystal was washed with 240 ml of cold water. Hydrated crystal obtained was dried in a rotary evaporator at 70° C. for 20 minutes under reduced pressure of 50 mmHg to obtain crude methacrylamide.

Crystallization: (recycle-1)

The same crystallization procedures as described above were carried out by using the crude methacrylamide obtained above to prepare pure methacrylamide. The yield and analytical results of pure methacrylamide are illustrated in Table 1.

In addition, the whole amount of the mother liquor thus obtained was treated by the same crystallization procedures described above and the resulting liquid was recycled to the next preparation step of crude methacrylamide.

Crystallization: (recycle-2 to 5)

The same procedures as described in the above crystallization (recycle-1) was repeated to obtain pure methacrylamide. The yield and analytical results of pure methacrylamide are illustrated in Table 1.

Reduction in the yield and quality of pure methacrylamide caused by the recycle of the whole amount of mother liquor was not found at all.

EXAMPLE 2

Crystallization

Crude methacrylamide was prepared by carrying out the same procedures as described in Example 1, (Synthesis of crude methacrylamide raw material).

By using the crude methacrylamide, crystallization was carried out by repeating the procedures as described in Example 1, (Crystallization) to obtain 142 g of pure methacrylamide.

The pure methacrylamide had purity of 99.5% or more, moisture content of 0.4%, Hazen number (APHA) of 10 or less, and transparency of 50 or more.

In addition, 270 g of the mother liquor having a methacrylamide concentration of 17% was obtained.

By using a half amount of the mother liquor, pH adjustment, separation of insoluble matter, and recycle to the preparation step of crude methacrylamide were carried out as described in Example 1, (Crystallization).

The other half of the mother liquor was used as intact for a portion of the dissolving solution of the crude methacrylamide in the next crystallization step.

Crystallization: (recycle-1)

To a 3 l flask equipped with a stirrer, 864 ml of water and 132 g of the above treated mother liquor were charged, and 670 g of methacrylamide sulfate described in Example 1, Synthesis-1 (crude methacrylamide raw material) was added dropwise at temperature of 30° C. or less.

Successively, the same procedures as described in Example 1, (Synthesis of crude methacrylamide raw material) were carried out to prepare crude methacrylamide.

In the next step, to a 1 l flask equipped with a stirrer, 108 ml of water and 135 g of the untreated mother liquor were charged, warmed to 50° C., and the crude methacrylamide was added so as to obtain a concentration of 47%.

Successively, by using the solution, crystallization was carried out as described in Example 1, (Crystallization) to prepare pure methacrylamide.

The yield and analytical results of the pure methacrylamide obtained are illustrated in Table 1.

In addition, the mother liquor obtained had a methacrylamide concentration of 17%.

By using a half of the mother liquor, pH adjustment, separation of insoluble matter, and recycle to the preparation step of crude methacrylamide were carried out as described in Example 1, (Crystallization).

The other half of the mother liquor was used as intact for a portion of the crude methacrylamide dissolving solution in the next crystallization step.

Crystallization: (recycle-2 to 5)

Pure methacrylamide was prepared by repeating the same procedures as described in the above Crystallization (recycle-1). The yield and analytical results are illustrated in Table 1.

Reduction in the yield and quality of pure methacrylamide caused by the recycle of a half amount of mother liquor was not found at all.

COMPARATIVE EXAMPLE 1

Crystallization: (recycle-0)

Pure methacrylamide was prepared by carrying out the same procedures as described in Example 1, (Synthesis of crude methacrylamide raw material) and (Crystallization). The yield and analytical results of pure methacrylamide obtained are illustrated in Table 1.

In addition, the whole amount of the mother liquor obtained was recycled as intact to the next preparation step of crude methacrylamide.

Crystallization: (recycle-1)

Crude methacrylamide was prepared by carrying out the same procedures as described in Example 1, (Synthesis-1) (crude methacrylamide raw material) except that the untreated mother liquor was used.

Pure methacrylamide was obtained by carrying out the same procedures as described in Example 1, (Crystallization). The yield and analytical results are illustrated in Table 1.

In addition, the whole amount of the mother liquor obtained was recycled as such to the next preparation step of crude methacrylamide.

Crystallization: (recycle-2 to 5)

Pure methacrylamide was prepared by carrying out the same procedures as described in the above (Crystallization) (recycle-1).

The yield and analytical results are illustrated in Table 1.

When the whole amount of the mother liquor was recycled 4 times or more, the quality of methacrylamide deteriorated.

COMPARATIVE EXAMPLE 2

Crystallization: (recycle-0)

Pure methacrylamide was prepared by carrying out the same procedures as described in Example 1, (Synthesis of crude methacrylamide raw material) and (Crystallization).

The yield and analytical results of pure methacrylamide obtained are illustrated in Table 1.

In addition, the mother liquor obtained was recycled as such to the next crystallization step to use as a portion of crude methacrylamide dissolving solution.

Crystallization: (recycle-1)

Crude methacrylamide was prepared by carrying out the same procedures as described in Example 1, (Synthesis-1) (crude methacrylamide raw material).

By using the crude methacrylamide, pure methacrylamide was prepared by carrying out the same procedures as described in Example 1, (Crystallization) except that the mother liquor was used as a portion of crude methacrylamide dissolving solution.

The yield and analytical results of methacrylamide obtained are illustrated in Table 1.

In addition, the mother liquor obtained was recycled as intact to the next crystallization step to use as a portion of methacrylamide dissolving solution.

Crystallization: (recycle-2 to 5)

Pure methacrylamide was prepared by repeating the same procedures as described in the above (Crystallization) (recycle-1).

The yield and analytical results are illustrated in Table 1.

When the mother liquor is recycled 4 times or more, quality of methacrylamide was deteriorated.

TABLE 1

| | Number of recycle | Yield (g) | Purity (%) | Hazen number (APHA) | Transparency |
|---|---|---|---|---|---|
| Example 1 | 1 | 142 | 99.5< | <10 | 50< |
| | 2 | 140 | " | " | " |
| | 3 | 138 | " | " | " |
| | 4 | 141 | " | " | " |
| | 5 | 139 | " | " | " |
| Example 2 | 1 | 138 | 99.5< | <10 | 50< |
| | 2 | 140 | " | " | " |
| | 3 | 141 | " | " | " |
| | 4 | 139 | " | " | " |
| | 5 | 139 | " | " | " |
| Comparative Example 1 | 0 | 140 | 99.5< | <10 | 50< |
| | 1 | 142 | " | " | " |
| | 2 | 136 | " | " | " |
| | 3 | 137 | " | " | " |
| | 4 | 135 | " | 15 | 38 |
| | 5 | 133 | " | 20 | 25 |
| Comparative Example 2 | 0 | 143 | 99.5< | <10 | 50< |
| | 1 | 140 | " | " | " |
| | 2 | 139 | " | " | " |
| | 3 | 135 | " | " | " |
| | 4 | 135 | " | 15 | 40 |
| | 5 | 132 | " | 15 | 31 |

EXAMPLE 3

Crystallization: (recycle-0)

To a 2 l flask equipped with a stirrer, 550 ml of water was charged and warmed to 50° C. Crude methacrylamide was added so as to obtain a concentration of 47%. To the solution thus obtained, a 48% aqueous sodium hydroxide solution was added to adjust the solution of pH 10.

The aqueous methacrylamide solution obtained was allowed to cool for 30 minutes, and thereafter cooled to 15° C. over 30 minutes to precipitate the crystal.

The resulting slurry was sufficiently centrifuge-dehydrated and the crystal was washed by spraying 100 ml of cold water.

The hydrate crystal obtained was dryed in a rotary evaporator at 60° C. under air blowing to obtain 360 g of pure methacrylamide.

The pure methacrylamide had purity of 99.5% or more, moisture content of 0.4%, Hazen number (APHA) of 10 or less, and transparency of 50 or more.

In addition the mother liquor obtained was 670 g and had a methacrylamide concentration of 17%.

The whole amount of the mother liquor was charged to a 1 l flask equipped with a stirrer and adjusted to pH 3 by using 98% sulfuric acid. Precipitated insoluble matter was filtered off with a nutsche fitted with a celite-precoated filter paper.

Successively, the liquid thus obtained was passed at a rate of 1 (/hr through a column which had a diameter of 20 mm and a length of 1 m and was packed with 200 ml of strongly basic anion exchange resin Lewatit MP-500 (Trade Mark of Bayer AG).

Crystallization: (recycle-1)

To a 2 l flask equipped with a stirrer, 630 g of the treated mother liquor having pH 10 obtained above was charged, 23 ml of water was added, and further crude methacrylamide was added and dissolved to obtain a solution having a concentration of 47%.

Successively, pure methacrylamide was prepared by carrying out the same procedures as described in (Crystallization) (recycle-0).

The yield and analytical results of the pure methacrylamide obtained are illustrated in Table 2.

In addition, the whole amount of the mother liquor was treated by the same procedures as described in (Crystallization) (recycle-o) and used for the next crystallization step.

Crystallization: (recycle-2 to 5)

Recycle of the mother liquor was carried out by the same procedures as described in (Crystallization) (recycle-1) to obtain pure methacrylamide.

The yield and analytical results of the pure methacrylamide are illustrated in Table 2.

EXAMPLE 4

Crystallization: (recycle-1)

Crystallization was carried out by the same procedures as described in Example 3, (Crystallization) (recycle-0).

By using half of the mother liquor obtained, pH adjustment, filtration of insoluble matter, and treatment with anion exchange resin were carried out. The treated mother liquor obtained was mixed with untreated mother liquor.

By using the mixture thus obtained, the same procedures as described in Example 3, (Crystallization) (recycle-1) was carried out to obtain pure methacrylamide.

The yield and analytical results of the pure methacrylamide obtained are illustrated in Table 2.

Further, a half amount of the mother liquor was treated by the same procedures as described in Example 3, (Crystallization) (recycle-0). The treated mother liquor obtained was mixed with untreated mother liquor and used for the next crystallization step.

Crystallization: (recycle-2 to 5)

Recycle of the mother liquor was carried out by the same procedures as described in (Crystallization) (recycle-1) to obtain pure methacrylamide.

The yield and analytical results of the pure methacrylamide are illustrated in Table 2.

COMPARATIVE EXAMPLE 3

Pure methacrylamide was prepared by carrying out the same procedures as described in Example 3 except that treatment of the mother liquor obtained was omitted.

The yield and analytical results of the pure methacrylamide obtained are illustrated in Table 2.

COMPARATIVE EXAMPLE 4

The same procedures as described in Example 3 were carried out except that 2% by weight of the mother liquor obtained was subjected to pH adjustment, filtration of insoluble matter, and treatment with anion exchange resin as described in Example 3. The treated mother liquor obtained was mixed with untreated mother liquor.

By using the mixture thus obtained, the same procedures as described in Example 3, (Crystallization) (recycle-1) were carried out to obtain pure methacrylamide.

Further, 2% by weight of the mother liquor obtained was treated by the same procedures as described in Example 3. The treated mother liquor thus obtained was mixed with untreated mother liquor and used for the next crystallization step. The recycle was repeated 5 times. The results are illustrated in Table 2.

TABLE 2

| | Number of recycle | Yield (g) | Purity (%) | Hazen number (APHA) | Transparency |
|---|---|---|---|---|---|
| Example 3 | 1 | 355 | 99.5< | <10 | 50< |
| | 2 | 362 | " | " | " |
| | 3 | 350 | " | " | " |
| | 4 | 353 | " | " | " |
| | 5 | 355 | " | " | " |
| Example 4 | 1 | 353 | 99.5< | <10 | 50< |
| | 2 | 360 | " | " | " |
| | 3 | 358 | " | " | " |
| | 4 | 355 | " | " | " |
| | 5 | 350 | " | " | " |
| Comparative Example 3 | 1 | 352 | 99.5< | <10 | 50< |
| | 2 | 348 | " | " | " |
| | 3 | 353 | " | " | 45 |
| | 4 | 347 | " | 15 | 37 |
| | 5 | 345 | " | 15 | 20 |
| Comparative Example 4 | 1 | 355 | 99.5< | <10 | 50< |
| | 2 | 354 | " | " | " |
| | 3 | 348 | " | " | " |
| | 4 | 357 | " | 10 | 41 |
| | 5 | 345 | " | 15 | 29 |

In the case of adjusting a portion of crystallization mother liquor to pH 5 or less, separating the precipitated insoluble matter, and reusing the treated mother liquor by using the process of the present invention, the pure methacrylamide obtained by recycling the crystallization mother liquor 5 times or more does not have any deterioration in the Hazen number and transparency.

On the other hand, when the removal of insoluble matter by pH adjustment is omitted, deterioration was clearly found after recycling from 3 to 4 times.

What is claimed is:

1. A purification process of crude methacrylamide by recrystallization from an aqueous methacrylamide solution obtained by neutralizing methacrylamide sulfate with a basic compound, comprising the steps of conducting crystallization by adjusting the hydrogen ion concentration of the aqueous methacrylamide solution to between pH 8 and pH 13, separating methacrylamide crystal, adjusting 5% or more by weight of the resulting mother liquor to between pH 1 and pH 5, separating precipitated insoluble matter, and recycling the thus-treated mother liquor to the neutralization step.

2. The purification process of claim 1 wherein from 10 to 80% by weight of the mother liquor is adjusted to between pH 1 and pH 5.

3. The purification process of claim 1 wherein from 10 to 80% by weight of the mother liquor is recycled to the neutralization step and from 90 to 20% by weight of the mother liquor is recycled to a dissolution step of crude methacrylamide.

4. The purification process of claim 1 wherein the pH of the mother liquor is adjusted to between pH 1 and pH 5 by using mineral acid selected from the group consisting of sulfuric acid and hydrochloric acid.

* * * * *